United States Patent [19]

Giudice et al.

[11] Patent Number: 4,489,079

[45] Date of Patent: Dec. 18, 1984

[54] PHARMACEUTICAL COMPOSITIONS HAVING A PERIPHERAL ANTAGONISTIC ACTION WITH RESPECT TO OPIATES

[75] Inventors: Antonina Giudice, Milan, Italy; Claude Moulineau, Montpellier, France; Luciano Manara, Pietra Marazzi; Paolo Carminati, Milan, both of Italy

[73] Assignee: Sonofi, Paris, France

[21] Appl. No.: 422,568

[22] Filed: Sep. 24, 1982

[30] Foreign Application Priority Data

Oct. 19, 1981 [FR] France .................. 81 19607

[51] Int. Cl.$^3$ .......................... A61K 31/485
[52] U.S. Cl. ............................ 424/260
[58] Field of Search ........................ 424/260

[56] References Cited

U.S. PATENT DOCUMENTS 4,176,186 11/1979 Goldberg et al. ........... 424/260

OTHER PUBLICATIONS

Helvetica Chimica Acta, vol. 39, pp. 429–440.

Primary Examiner—Stanley J. Friedman
Attorney, Agent, or Firm—Lewis H. Eslinger

[57] ABSTRACT

The present invention relates to a pharmaceutical composition having a peripheral antagonistic action with respect to opiates containing, as active ingredient, a haloallylate of levallorphan of formula:

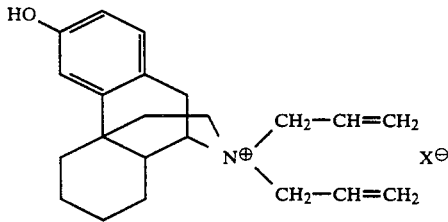

where X is chlorine, bromine or iodine, mixed with a pharmaceutical excipient.

2 Claims, No Drawings

PHARMACEUTICAL COMPOSITIONS HAVING A PERIPHERAL ANTAGONISTIC ACTION WITH RESPECT TO OPIATES

The present invention relates to a pharmaceutical composition having a peripheral antagonistic action with respect to opiates.

More particularly, the present invention relates to a pharmaceutical composition in dosage unit form containing a haloallylate of levellorphan of formula:

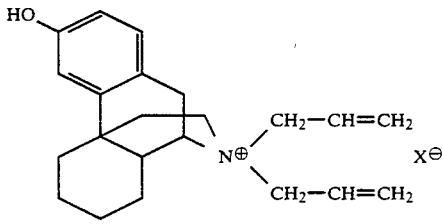

where X is chlorine, bromine or iodine, mixed with a pharmaceutical excipient.

Despite the various problems associated with the use of opiates, such as tolerance and physical dependence, drugs containing morphine remain without equal in the treatment of violent pain.

An often serious secondary effect of morphinic drugs is constipation, which is due to the local action thereof on the intestinal opiate receptors.

To overcome this type of secondary effect, which is distressful to the patient, it has been proposed that an antagonist of narcotics having a weak capacity of penetration through the haematoencephalic barrier could significantly reduce the constipation provoked by the morphinic drugs without substantially reducing the analgesic effects thereof.

U.S. Pat. No. 4,176,186 describes quaternary derivatives of morphinic antagonists which prevent or eliminate the secondary effects of opiates on the intestinal motility. Among the compounds claimed by the aforementioned Patent, the preferred compounds are the quaternary derivatives of N-allylnoroxymorphone, hereinafter called "naloxone", of which the bromomethylate is particularly preferred.

It has now been found that the haloallylates of levallorphan of formula I hereinabove have a virtually zero capacity of penetration of the haematoencephalic barrier, whilst maintaining a good peripheral antagonistic activity.

More particularly, it has been found that the haloallylates of levallorphan of formula I hereinabove do not antagonise the the analgesic effect of morphine, whilst they antagonise the constipating effect thereof.

Table I hereinbelow shows the activity of the haloallylates of levallorphan as antagonists of the constipating and analgesic effects of morphine in comparison with the corresponding action of a well known antagonist of narcotics, naloxone, as well as of the sulfomethylate and bromomethylate of naloxone described in U.S. Pat. No. 4,176,186.

The antagonism to the constipating effect of morphine was assessed according to the test described by A. F. Green, Brit. J. Pharmacol. 1959, 14, 26, after opportune modification.

Three groups of female mice of about 20 grams are used, having fasted for 20 hours. To a control group is administered by the oral route a meal constituted by 0.2 ml of a mixture of 5% gum arabic (6 ml), flour (2 g) and charcoal (1 g). To the second group is administered by the subcutaneous route 12 mg/kg of morphine and, immediately afterwards, the above meal including charcoal. The third group is treated with the antagonist under examination by the subcutaneous route, then, after 5 minutes, with 12 mg/kg of morphine by the subcutaneous route and, immediately afterwards, with the meal including charcoal. Thirty minutes afterwards, the animals are sacrificed to assess the portion of intestine through which the charcoal has passed, expressed as % of the total length of the small intestine.

The antagonism to the analgesic effect of morphine was assessed according to the conventional test for analgesia of electrostimulation of the tail in the mouse.

Female mice of 18 to 20 grams are used. The animals, having fasted for 18 hours, are placed in small cages placed on a special tray, so that their tails can emerge through an appropriately made hole and rest on the tray. Two needles are inserted in each animal's tail, the first 1 cm from the root of the tail and the other 2 cm from the first needle. The two electrodes are connected to a Grass S 48 electrostimulator with which is sought the minimum voltage which, at the frequency of 20 puls./sec. of the duration of 5 milliseconds and for 1 minute, determines the reaction characterised by a cry of pain. After having established the threshold of sensitivity, the animals are treated with the substance to be examined and at pre-established intervals, they are stimulated again to find the new threshold. A group of control animals is treated with morphine by the subcutaneous route at a dose of 12 mg/kg, which determines on 100% of the animals an average increase of 100% of the threshold of sensitivity. Another group of animals is treated with the substance under examination by the subcutaneous route and, 5 minutes afterwards, morphine is injected by the subcutaneous route at the dose of 12 mg/kg. The antagonism to the analgesic action of morphine is assessed on the basis of the percentage of inhibition of the analgesic effect of morphine on the animals treated with respect to the controls.

The activity of the substances having a peripheral antagonistic activity with respect to narcotics is assessed on the basis of the inhibition percent of the constipating effect and of the analgesic effect of morphine. The dose which inhibits said effects by 50% ($ID_{50c}$ for the constipating effect and $ID_{50a}$ for the analgesic effect) has been extrapolated from the least squares line log dose-response by applying the analysis of the variance by linear regression.

TABLE I

| Compound | Antagonism with respect to the constipating effect $ID_{50c}$ | Antagonism with respect to the analgesic effect $ID_{50a}$ | $ID_{50a}/ID_{50c}$ |
|---|---|---|---|
| levallorphan chloroallylate | 27.30 mg/kg (12.00–62.00) | >140 mg/kg (°) | >5.12 (°) |
| levallorphan bromoallylate | 15.65 mg/kg (8.46–28.9) | >80 mg/kg (°) | >5.11 (°) |
| levallorphan iodoallylate | 16.68 mg/kg (8.23–33.80) | >60 mg/kg (°) | >3.61 (°) |
| naloxone bromomethylate | 10.81 mg/kg (6.2–18.8) | 5.117 mg/kg (1.3–19.7) | 0.47 |
| naloxone sulfomethylate | 2.99 mg/kg (1.51–5.92) | 5.039 mg/kg (1.8–14.0) | 1.68 |
| naloxone | 0.75 mg/kg | 0.083 mg/kg | 0.11 |

TABLE I-continued

| Compound | Antagonism with respect to the constipating effect $ID_{50c}$ | Antagonism with respect to the analgesic effect $ID_{50a}$ | $ID_{50a}/ID_{50c}$ |
| --- | --- | --- | --- |
| | (0.46–1.23) | (0.02–0.24) | |

(*) inactive up to the maximum injectable dose

This Table shows that the compounds used as active ingredients in the pharmaceutical compositions of the present invention antagonise the constipating effect of morphine with an $ID_{50c}$ of 15.65 to 27.30 mg/kg whilst, up to the maximum injectable doses, they do not antagonise the analgesic effect of morphine. On the other hand, the quaternary derivatives of the naloxone described in U.S. Pat. No. 4,176,186, most active of the haloallylates of levallorphan as antagonists of the constipating action, antagonise the analgesic effect of morphine with an $ID_{50a}$ which is fairly close to the $ID_{50c}$. For its part, the naloxone is much more active as antagonist of the analgesic effect than antagonist of the constipating effect.

It follows that the active ingredient compounds of the pharmaceutical compositions of the present invention do not manifest central effects up to the maximum injectable dose, thus showing virtually pure peripheral antagonists, whilst, among the reference compounds, the bromomethylate and sulfomethylate of naloxone have a certain central activity and the naloxone itself is very active, thus confirming its capacity of excellent central antagonist.

The bromoallylate of levallorphan is described, with its physico-chemical constants, by J. Hellerbach, O. Schnider, H. Besendorf and B. Pellmont in Synthetic Analgesics, Publishers D. H. R. Barton and W. Von Doering, Pergamon Press, 1974, part II, page 48, in a summary table, but no reference to the chemical synthesis of the product nor to the pharmacological properties thereof is indicated by the authors. The same authors indicate, in reference n. 180, page 108 of the same book, that the data relative to the product have not been made public. The chloro- and iodoallytes are novel.

The haloallylates of levallorphan are prepared by reaction of a halide of allyl on levallorphan in an organic solvent at a temperature of 50° to 100° C.

As reaction solvent, an aprotic polar solvent such as dimethylformamide, dimethylacetamide, dimethylsulfoxide and the like is used.

The final product is isolated according to conventional techniques by eliminating the solvent and taking up the haloallylate of levallorphan in an appropriate solvent.

The pharmaceutical compositions having a peripheral antagonistic action with respect to opiates, according to the present invention, are useful in the treatment of pathological conditions where there are altered rates of exogenous or endogenous opiates, or a hypersensitivity to opiates outside the central nervous system of mammals.

The compositions of the present invention may thus be administered to mammals, animals and human beings, with opiates in order to prevent the secondary effects thereof, especially constipation, which derive in particular from the activation of the receptors situated on the periphery, without compromising the analgesia, or any other action of the opiates, provoked by stimulation of the central receptors by the opiate.

In order to obtain the desired peripheral antagonistic effect, the dose of active ingredient may vary between 0.05 and 200 mg per kg of weight of the body and per day.

Each dosage unit may contain from 1 to 500 mg of active ingredient in combination with a pharmaceutical support. This dosage unit may be administered to the mammals 1 to 4 times per day.

The pharmaceutical compositions of the present invention having a peripheral antagonistic action with respect to opiates may be formulated for oral, sublingual, subcutaneous, intramuscular, intravenous, transdermal or rectal administration, by mixing the active ingredient of formula I hereinabove with conventional pharmaceutical supports.

The unitary forms of administration include tablets, capsules, powders, granules and oral solutions or suspensions, suppositories and ampoules used for parenteral administration.

When a solid composition in the form of tablets is prepared, the main active ingredient is mixed with a pharmaceutical medium such as gelatin, starch, lactose, magnesium stearate, talc, gum arabic or the like. The tablets may be coated with sucrose or other appropriate substances or they may be treated in another manner such that their activity is prolonged or delayed and that they continually release a predetermined quantity of active ingredient.

A preparation in capsule form is obtained by mixing the active ingredient with a diluent and by pouring the mixture obtained in soft or hard capsules.

A preparation in the form of a syrup or elixir may contain the active ingredient together with an acaloric sweetening agent, methylparaben and propylparaben as antiseptics, as well as an agent giving taste and an appropriate colorant.

Water-dispersible powders or granulates may contain the active ingredient mixed with dispersion agents or wetting agents, or suspension agents such as polyvinylpyrrolidone and the like, as well as with sweetening agents or taste correctors.

For rectal application, suppositories are prepared with binding agents melting at rectal temperature, for example cocoa butter or polyethyleneglycols.

For oral administration in drops or for parenteral administration, sterile, injectable aqueous suspensions, isotonic saline solutions or particular solutions are used, which contain pharmacologically compatible dispersion agents and/or wetting agents, for example propyleneglycol or butyleneglycol.

The active ingredient may also be formulated in the form of microcapsules, possibly with one or more supports or additives.

The compositions of the present invention may contain, in addition to the haloallylate of levallorphan, other active ingredients such as for example narcotic analgesics such as morphine, codeine, buprenorphine and the like, antitussives or other appropriate drugs.

The following examples illustrate the invention without, however, limiting it.

EXAMPLE 1

A mixture of 1.2 g of levallorphan, 20 ml of anhydrous dimethylformamide and 0.98 g of allyl bromide is heated for 4 hours at 70° C. away from humidity. After elimination of the dimethylformamide, the gum obtained is triturated in 30 ml of acetone and, after 3 hours at 0° C., the solid is drained, washed with acetone and dried under reduced pressure at 90° C. 1.1 g of bromoallylate of levallorphan is thus obtained; m.p. 197°–198° C.

EXAMPLE 2

Tablets having the following composition are prepared:

| bromoallylate of levallorphan | 50 mg |
|---|---|
| lactose | 145 mg |
| avicel | 100 mg |
| magnesium stearate | 5 mg | by crushing the active ingredient to a particle dimension of 0.4 mm, passing it through a 0.4 mm mesh sieve, mixing the crushed substance with the other constituents and compressing the product to form the tablets.

Similarly, tablets containing 40 mg of bromoallylate of levallorphan are prepared.

EXAMPLE 3

Capsules are prepared based on bromoallylate of levallorphan having the following composition:

| bromoallylate of levallorphan | 15 mg |
|---|---|
| lactose | 120 mg |
| magnesium stearate | 5 mg | by intimately mixing the above ingredients and pouring the mixture in capsules of hard gelatin.

In the same way, capsules are prepared, containing 25 mg of bromoallylate of levallorphan.

EXAMPLE 4

10,000 capsules with a content of active substance of 50 mg are prepared from the following constituents: 500 g of bromoallylate of levallorphan, 495 g of microcrystalline cellulose, 5 g of amorphous silica gel. The above constituents are mixed well and introduced into capsules of hard gelatin of dimension 4.

EXAMPLE 5

A sterile aqueous solution appropriate for parenteral use in ampoules, having the following composition, is prepared:

| bromoallylate of levallorphan | 10 mg |
|---|---|
| water for injectable preparation q.s.p. | 2 ml |

EXAMPLE 6

Suppositories are prepared, having the following composition:

| bromoallylate of levallorphan | 50 mg |
|---|---|
| lactose | 250 mg |
| Witespol W 45 q.s.p. | 1.7 g |

The active substance is mixed with the lactose and the mixture is placed uniformly in suspension in the molten mass for suppositories. The suspension is poured into cooled moulds to form suppositories weighing 1.7 g.

EXAMPLE 7

Sugar-coated tablets each containing 30 mg of bromoallylate of levallorphan are prepared, using as excipient talc, lactose, corn starch, sodium alginate, caster sugar, granulated sugar, magnesium stearate, white shellac, gelatin for food, erythrosin, titanium dioxide and white wax.

EXAMPLES 8 AND 9

By treatment of the levallorphan with allyl chloride and allyl iodide, respectively, in dimethylformamide according to the modus operandi described in Example 1, the following is obtained: chloroallylate of levallorphan, a white solid having a m.p. of 240° to 245° C. (dec); and iodoallylate of levallorphan, a brown solid having a m.p. of 225° to 230° C. (dec), respectively.

EXAMPLES 10 TO 15

By operating as described in Examples 2 to 7, the following are prepared:
tablets containing 50 or 40 mg of chloroallylate of levallorphan,
capsules containing 15 or 25 mg of chloroallylate of levallorphan,
capsules containing 50 mg of chloroallylate of levallorphan,
ampoules containing 10 mg of chloroallylate of levallorphan,
suppositories containing 50 mg of chloroallylate of levallorphan,
sugar-coated tablets containing 30 mg of chloroallylate of levallorphan.

EXAMPLE 16

Sugar-coated tablets each containing 35 mg of iodoallyl of levallorphan are prepared, using as excipient talc, lactose, corn starch, sodium alginate, caster sugar, granulated sugar, magnesium stearate, white shellac, gelatin for food, erythrosin, titanium dioxide and white wax.

What is claimed is:

1. A method for treating the secondary effects of opiates in mamallian hosts comprising administrating to said mammalian hosts a pharmaceutically effective amount of a halloallylate of a levallorphan of the formula:

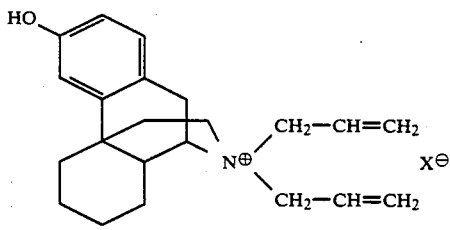

where x is chlorine, bromine or iodine.

2. A method of claim 1 where said haloallylate of levallorphan is administered to said mammalian host in amounts from about 1 to about 500 mg per dosage unit.